(12) United States Patent
Ravagnan et al.

(10) Patent No.: US 11,554,132 B2
(45) Date of Patent: Jan. 17, 2023

(54) COMPOSITIONS COMPRISING RESVERATROLOSIDES AND CURCUMINS

(71) Applicants: Giampietro Ravagnan, Rome (IT); Massimo Bonucci, Rome (IT)

(72) Inventors: Giampietro Ravagnan, Rome (IT); Massimo Bonucci, Rome (IT)

(73) Assignee: Giampietro Ravagnan, Rome (IT)

( * ) Notice: Subject to any disclaimer, the term of this patent is extended or adjusted under 35 U.S.C. 154(b) by 149 days.

(21) Appl. No.: 17/264,431

(22) PCT Filed: Aug. 1, 2019

(86) PCT No.: PCT/IB2019/056565
§ 371 (c)(1),
(2) Date: Jan. 29, 2021

(87) PCT Pub. No.: WO2020/026185
PCT Pub. Date: Feb. 6, 2020

(65) Prior Publication Data
US 2021/0308163 A1  Oct. 7, 2021

(30) Foreign Application Priority Data
Aug. 2, 2018 (IT) .................. 102018000007787

(51) Int. Cl.
| | | |
|---|---|---|
| *A61K 31/7034* | (2006.01) | |
| *A23L 33/125* | (2016.01) | |
| *A23L 33/00* | (2016.01) | |
| *A61P 35/00* | (2006.01) | |
| *A61K 9/00* | (2006.01) | |
| *A61K 31/12* | (2006.01) | |
| *A61K 31/4188* | (2006.01) | |

(52) U.S. Cl.
CPC ........ *A61K 31/7034* (2013.01); *A23L 33/125* (2016.08); *A23L 33/40* (2016.08); *A61K 9/006* (2013.01); *A61K 9/0043* (2013.01); *A61K 31/12* (2013.01); *A61K 31/4188* (2013.01); *A61P 35/00* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 10,485,768 B2 * | 11/2019 | Sordillo | A61K 31/4188 |
| 2006/0078631 A1 | 4/2006 | Newmark et al. | |
| 2012/0231097 A1 * | 9/2012 | Zhou | A61K 36/704 |
| | | | 514/35 |

OTHER PUBLICATIONS

Mukherjee et al., "Liposomal TriCurin, A Synergistic Combination of Curcumin, Epicatechin Gallate and Resveratrol, Repolarizes Tumor-AssociatedMicroglia/Macrophages, and Eliminates Glioblastoma (GBM) and GBM Stem Cells" Molecules 2018, v23, n 201, p. 1-21.
Pistollato et al., "Targeting Glioblastoma with the Use of Phytocompounds and Nanoparticles" Targeted Oncology, 2015, v 11, n 1, p. 1-16.
Li et al., "Resveratrol sensitizes glioblastoma-initiating cells to temozolomide by inducing cell apoptosis and promoting differentiation" Oncology Reports, 2015, 35, p. 343-351.
Lombardi et al., "Polydatin, a natural precursor of resveratrol, induces cell cycle arrest and differentiation of human colorectal Caco-2 cell" Journal of Translational Medicine, 2013, v 11, n 264, p. 1-11.

* cited by examiner

*Primary Examiner* — Dale R Miller
(74) *Attorney, Agent, or Firm* — Greer, Burns & Crain, Ltd.; Gregory P. Einhorn

(57) ABSTRACT

The invention refers to new methods for treating spontaneous tumors in humans of the Central Nervous System, more particularly of 3rd and 4th grade tumors, even more particularly gliomas, and is related to the administration of compositions comprising therapeutically effective amounts of resveratrolosides and curcumins, in particular natural extracts comprising said two components. The invention also relates to the realization of pharmaceutical and nutraceutleal compositions comprising resveratrolosides and curcumins More specifically, the invention relates to compositions formulated for the release of active components for sublingual administration.

17 Claims, 4 Drawing Sheets

Continuing the integrated treatment, only the outline can be appreciated 30 months later, regression is very good Reduced neoplastic residue
After 12 months of integrated treatment: further reduction

COMPOSITIONS COMPRISING RESVERATROLOSIDES AND CURCUMINS

This application is a national phase application claiming benefit of priority under 35 U.S.C. § 371 to Patent Convention Treaty (PCT) International Application serial number PCT/IB2019/056565, filed Aug. 1, 2019, which claims the benefit of priority to Italian patent No. 102018000007787 filed on Aug. 2, 2018. The aforementioned applications are expressly incorporated herein by reference in their entirety and for all purposes.

TECHNICAL FIELD

The present invention relates to novel methods to treat tumors of the Central Nervous System in humans (also referred to hereinafter as CNS), more particularly tumors of grade 3° and 4°, even more particularly glioblastoma (also referred to hereinafter to as GBL), and relates to the administration of compositions comprising therapeutically effective amounts of resveratrolosides (hereinafter also referred to as piceids) and curcumins, in particular natural extracts comprising said two components simultaneously. The invention also relates to the realization of pharmaceutical and nutraceutical compositions comprising resveratrolosides and curcumins. More specifically, the invention relates to compositions formulated for the release of the active components for sublingual administration.

The object of the present invention is to provide pharmaceutical and nutraceutical compositions with improved efficacy in the context of the protocols of integrated anticancer therapies. More particularly, the invention relates to tumors of the Central Nervous System in humans, even more particularly to tumors of grade 3° and 4°, with particular reference to glioblastoma. The improvement associated with the compositions according to the invention consists in controlling factors that lead to the progression of tumor pathologies with poor prognosis, such as glioblastoma.

The resveratrolosides to which the invention relates in particular are the glucosidic stilbenoids known with the names of piceid (CAS number 38963-95-0) and polydatin (CAS number 27208-80-6).

STATE OF ART

Tumors of the Central Nervous System (CNS) comprise a diverse set of pathological entities. Due to the fact that glia tumors alone account for almost 40% of all CNS tumors, in the literature it is customary to make a distinction between glia tumors (or gliomas) and non glia tumors.

Glia tumors include: astrocytomas (which originate from the astrocytic cells of the glia), oligodendrogliomas (from oligodendroglial cells) and ependymomas (from ependymal cells).

Different systems have been suggested for the gradation (of malignancy) of CNS tumors over time. Since 1993 the 4-level grading system proposed by the World Health Organization (WHO) has proved to be the most widely accepted and widespread. It is based on four histological features: nuclear atypia, presence of mitosis, endothelial proliferation, necrosis. Obviously tumors with the worst outcome are 3rd and 4th grade tumors. Among the 3rd grade tumors are anaplastic astrocytomas, among the 4th grade tumors are glioblastomas.

Glioblastoma is the most aggressive of the primitive brain tumors. It is among those defined as "orphan drugs" for which no cure exists https://www.osservatoriomalattiera-re.it/glioblastoma.

Despite the progress in neurosurgery and neuro-oncology, the survival of glioblastoma patients is short, on average only 15 months after diagnosis. This tumor affects about 1,500 Italians every year, with an incidence peak between 50 and 65 years.

Glioblastoma is produced by aberrant stem cells that, instead of generating a normal tissue, give rise to a highly malignant brain tumor. Unlike other tumors, an early diagnosis that leads to healing is not possible in glioblastoma. Glioblastoma stem cells in fact, in addition to being resistant to drug therapies, have the ability to migrate from the tumor and spread to different brain areas. This is why surgical therapy only manages to prolong survival, but it never brings healing to those suffering from this disease.

GBL-tumorigenesis is characterized by a high production of lipids derived from arachidonic acid. These molecules stimulate the development of the peritumoral cerebral edema and tumor progression. Glucocorticoids are the most effective drugs currently used for the treatment of cerebral edema, but they are associated with numerous side effects. Since the available therapies are not very effective, over 50% of GBL-patients use complementary and alternative approaches, among which herbal therapies are the most commonly used, but with little success.

Glucosidic stilbenoids, also called piceids, and curcumins are compounds that can be natural or synthetic. The natural sources are mainly grapes, polygonacee (for example, *Fallopia japonica*) and turmeric, from which they can be extracted by known methods (EP1292319, "Botanicals, a Phytocosmetic Desk Reference" Frank S. D'Amelio, CRC Press, pgs. 39-48). Both piceids and curcumins are widely used alone or in combination with each other in the pharmaceutical field, such as drugs, and in the nutraceutical field, as food supplements.

US 2009/0047371 describes the use of resveratrol and curcumin compositions for the treatment of prostate tumors and other inflammatory-based diseases, such as psoriasis and skin diseases, but there are no indications that the piceid and curcumin combination can be used for the treatment of tumors of the Central Nervous System (CNS).

WO 2015/081319 describes the use of resveratrol and curcumin compositions for the in vitro and in vivo treatment of virus dependent cervix tumors, however there are neither indications that the piceid and curcumin combination can be used for the treatment of tumors of the Central Nervous System (CNS), nor are there indications relating to trials on humans.

U.S. Pat. No. 7,931,922 describes the use of natural multi-component compositions with COX-2 inhibition effect for the treatment of GBL, however the reported experimentation is related to oral administrations. Certainly the chemical structure that characterizes polydatin, makes an in se simple, fast and quantitatively relevant passage of the molecule circulating with an important bio-available portion compared to resveratrol. However, the greater difficulty in the therapeutically effective use of curcumins and resveratrol is related to their poor bio-availability. In fact, after an oral administration both resveratrol molecules and curcumins have difficulties of intestinal absorption, as well as being subject to a degradation during their passage in the liver. For such reasons just therapeutically ineffective levels are found in blood. In order to have a therapeutic effect, very high dosages should be used, but this leads to undesirable effects such as epigastric pain and/or diarrhea.

Known compositions based on resveratrol and/or resveratrolosides and curcumin in the treatment of glioblastoma are carried in the form of liposomes since, as is known, curcumin and resveratrol are absorbed with difficulty in the intestine. The tests reported in the literature are only either in vitro or in vivo tests on animals to which the tumor was grafted. Actually, the efficacy of said compositions on spontaneous tumors in man was never tested, that is, there is no clinical evidence that such compositions can be effective on humans, nor a sublingual administration has ever been described or deducible from the prior art.

In addition, it is a fact that no real therapeutic efficacy on humans can be deduced from in vitro or animal tests, as any encouraging data is not a reasonable expectation of success, not being it possible to make an objective scientific assessment of available data. The obviousness is not only at hand when the results are clearly predictable, but also when there is a reasonable expectation of success and even if it were evident to the person skilled in the art to try an experiment against potentially encouraging data, it would not be necessarily true for the expert to have reasonable expectations of success by transferring the evidence obtained in the laboratory to clinical trials, i.e on real patients.

Therefore, although the combinations (resveratrol and/or piceid)+curcumin are known in the treatment of tumors, from the teachings of the known art the indication or suggestion that these combinations are really effective on humans is not derived, nor that formulations different from the oral ones are particularly effective in clinical experimentation to contrast CNS tumors.

Furthermore, there are currently no studies or work on the use of natural substances such as curcumin and/or polydatin in combination with conventional treatments (chemo+radiotherapy and/or biological therapy).

SUMMARY OF THE INVENTION

Often an active ingredient is poorly effective due to inadequate administration methods. An unexpected synergistic effect has now been found regarding the combination of piceids+curcumins in the treatment of CNS tumors, in particular tumors grade 3rd and 4th, more particularly gliomas, even more particularly glioblastoma; this unexpected synergistic effect is particularly evident when the compositions are formulated for sublingual administration. Sublingual administration is also more advantageous and useful than an equivalent administration by injection. Not to mention that in some countries, for example in Italy, the administration of curcumins by injection is illegal.

The combination of piceids and curcumins according to the invention has shown an unexpected synergistic effect, made evident also by the clinical results that occurred in patients suffering from glioblastoma, who showed a significant increase in their life expectancy.

It is therefore an object of the present invention a pharmaceutical and/or nutraceutical composition comprising therapeutically effective amounts of piceids and curcumins in combination with one another for use in the treatment of CNS tumors, in particular 3rd and 4th grade tumors, more particularly gliomas, even more particularly glioblastoma.

Another object of the invention is a pharmaceutical and nutraceutical composition designed to reduce the side effects associated with CNS tumors, in particular edema. For this purpose the composition of the invention can be administered in combination with other compounds with anti-edema activity, in particular compounds of vegetable origin, more particularly the *Boswelia serrata* extract.

Another object of the invention is a formulation comprising the association of piceids and curcumins for sublingual administration.

A further object of the invention is the use of the combination of piceids and curcumins according to the invention in association and integration to traditional oncologic therapies, such as surgery and/or chemotherapy or/and radiotherapy.

Still another object of the invention is a formulation comprising as an active ingredient the combination of piceids and curcumins in which piceid is polydatin (CAS number 27208-80-6) and curcumins are represented by curcumin, which in itself is a combination of Curcumin I, Curcumin II and Curcumin III.

Still a further object of the invention relates to a method for treating CNS tumors, in particular 3rd and 4th grade tumors, more particularly gliomas, even more particularly glioblastoma, in a subject human mammal, comprising the step of administering to said subject an effective amount of a composition to treat the tumor or prevent recurrence of said tumor, said composition comprising therapeutically effective amounts of piceids and curcumins in which piceid is polydatin (CAS number 27208-80-6) and curcumins are represented by curcumin, which in itself is a combination of Curcumin I, Curcumin II and Curcumin III.

A preferred aspect of the present invention relates to a method for treating side effects associated with glioblastoma in a subject, comprising the step of administering an effective amount of a composition to said subject in order to treat said side effects, said composition comprising therapeutically effective amounts of piceids and curcumins, alone or in combination in separate administration with anti-edema compounds.

Further aspects will become apparent from the detailed description of the invention.

BRIEF DESCRIPTION OF THE FIGURES

The present invention will be described hereinafter through some preferred embodiments, given only by way of a non-limiting example, with reference to the attached drawings.

FIG. 1: 70-year-old man with Glioblastoma. Integrated therapy consisting of: *Boswellia Serrata* for cerebral edema, Polydatin and Curcumin. The subject followed an adequate diet with control of protein, carbohydrate and fat intake. FIG. 1D, 30 months later. Regression is very good from December 2012 until today. By continuing the integrated treatment the damage is continuously reduced. The result achieved shows a complete regression of the damage with an integrated treatment, an unexpected result with a conventional treatment.

FIG. 2: Start of treatment 2015.

DETAILED DESCRIPTION OF THE INVENTION

Figure 1A:
FIG. 1A, Radiotherapy and Temodal (April 2011); malignant neoplasm that extensively affects the cerebral parenchyma.
Figure 1B:
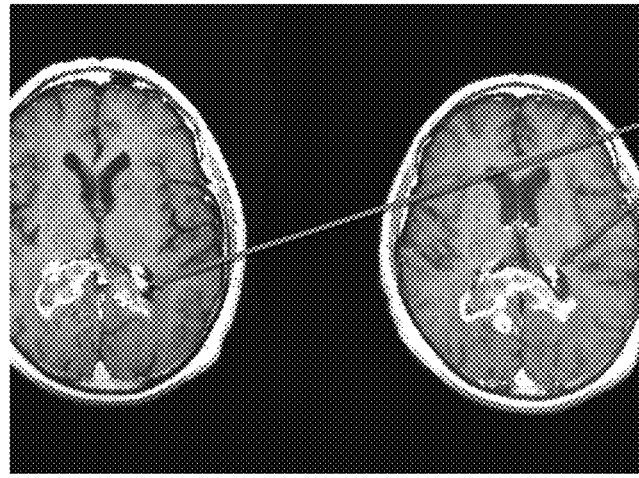
FIG. 1B, weekly Temodal (July 2011). After treatment with Radiotherapy and Temozolomide (three months) and integrated therapy (polidatin and curcumin according to the invention), neoplasm is greatly reduced.
Figure 1C:
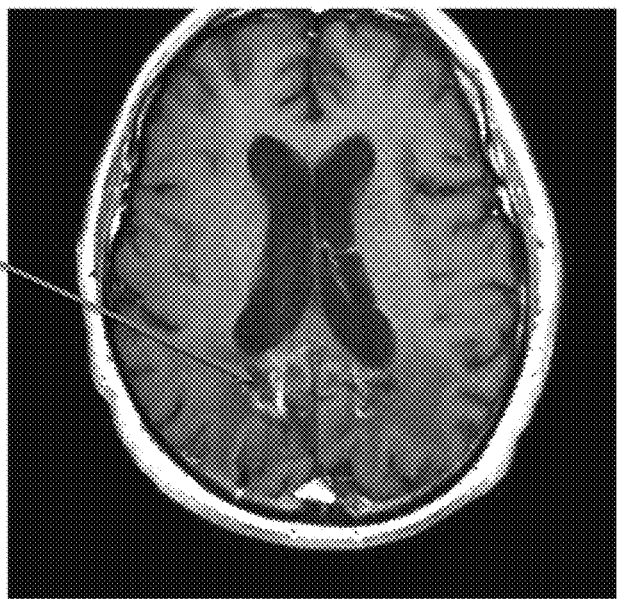
FIG. 1C, Continuing the integrated treatment of the invention, a clear further reduction can be noted: only the outline can be appreciated.
Figure 1D:
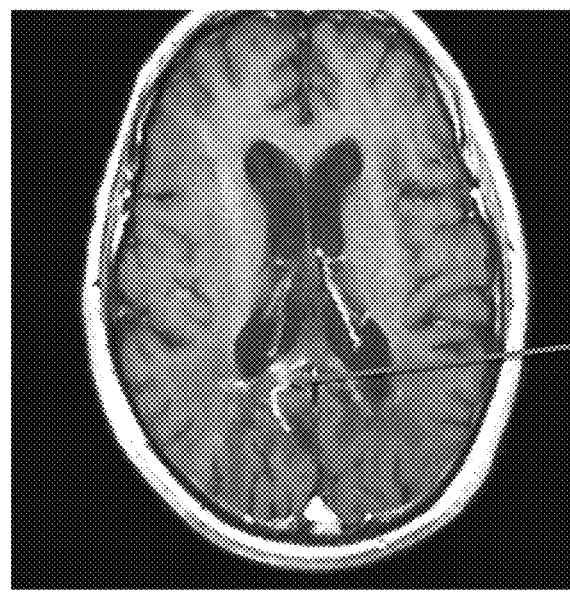
Figure 2A:
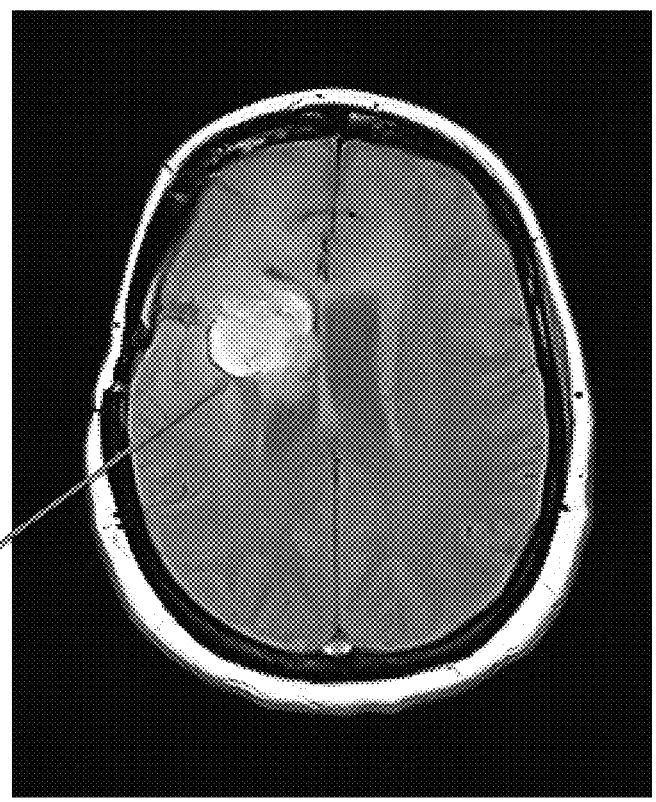
FIG. 2A: Neoplastic damage (in white) occurring in the cerebral parenchyma.
Figure 2B:
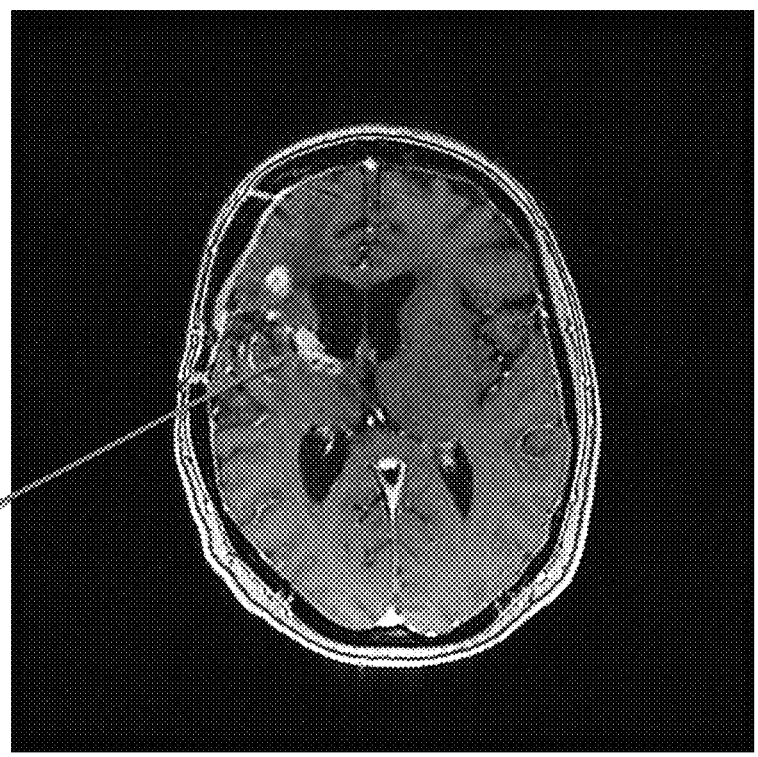
FIG. 2B: After treatment with Radiotherapy and chemotherapy with Temozolomide and integrated therapy with Curcumin, Polydatin and *Boswellia* (for cerebral edema) there is a clear reduction.
Figure 2C:
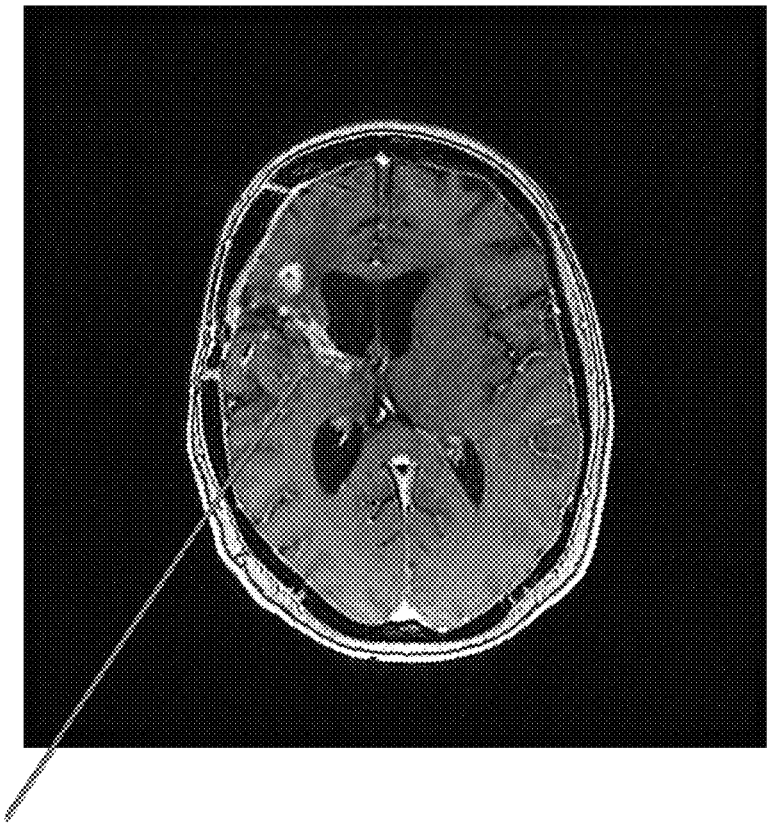
FIG. 2C: The residue is further reduced.

The term "therapeutically effective amount" as used herein refers to that amount of active ingredients which contributes to the ability of the composition of treating the tumor.

The term "treatment" as used herein refers to the partial or total inhibition of the growth, spread or formation of tumor metastases, in particular of glioblastoma, as well as to the partial or total destruction of the cancer cells. The term "treatment" includes the reduction or physiological elimination of the tumor (apoptosis), in particular of glioblastoma, and also the reduction of the incidence of the disease and its side effects. The terms "to prevent" and "prevention" as used herein will refer both to the prevention of the onset of a tumor, and to prevent the onset of a pre-clinically evident stage of it in individuals at risk. It also relates to the prevention of relapses of the neoplasm, namely the growth of malignant glia cells after removal of the damage. This definition refers to the prevention or the beginning of malignant cells proliferation and to stopping or reversing the progression of pre-malignant cells to malignant cells. The term "to prevent" also includes the prevention of tumor growth or spread, in particular of glioblastoma. This includes the prophylactic treatment of those persons who are subjected to environmental and/or family risk of developing the tumor, particularly glioblastoma.

The term "glioblastoma" as used herein generally refers to tumors of neuroglia cells and other malignant tumors or glia neoplasms of the Central Nervous System.

The term "subject" as used herein refers to any human mammal subject that has a CNS tumor, particularly glioblastoma, including children and pediatric subjects in general. For prevention methods, the subject is any human subject who is subjected to family and/or environmental risks of developing the tumor, particularly glioblastoma. The subject may be at risk due to exposure to carcinogens chemical and/or physical agents and/or can be genetically predisposed to develop a glioblastoma and in general CNS tumors. The subject may be at risk after the removal of both low grade (1st and 2nd) glia tumors and 3rd and 4th grade tumors and in particular glioblastoma. Glioblastoma has a high incidence of both local and metastatic relapses.

The terms "Integrated Oncology Therapy" and "integrated treatment" as used herein refer in general to the combination of conventional treatments such as surgery and/or chemotherapy and/or radiotherapy in association with therapeutically efficient amounts of the compositions of the invention, alone or in combination with other active ingredients commonly used as support therapy in the oncologic therapeutic field.

According to the present invention, with the term resveratrolosides or piceids, which are to be considered as being synonymous, a class of compounds is meant mainly of natural origin which have a trans-stilbenic glucosidate nucleus containing one or more hydroxyl groups variously distributed on the trans-stilbenic nucleus and which can be used in the composition of the invention alone or in a mixture with each other. These are molecules of natural origin in the class of stilbenoid glucosides of the general formula (I):

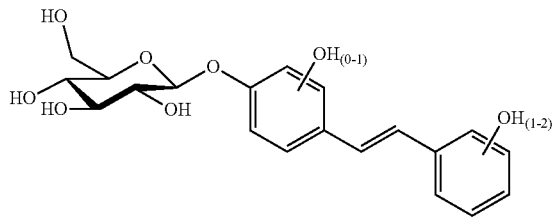

(I)

wherein the benzene groups are substituted with a number of hydroxyls variable between 1 and 3.

They can be obtained by chemical synthesis or by extraction from natural sources, according to known techniques. Some of the preferred glycoside stilbenoids to which the invention relates are represented by the following structural formula (I); they can be used in the composition of the invention, alone or in mixture with one another.

Particularly preferred compounds are indicated below.

Resveratroloside—(2S,3R,4S,5S,6R)-2-(4-((E)-3,5-dihydroxystyryl)phenoxy)-6-(hydroxymethyl)tetrahydro-2H-piran-3,4,5-triol—(CAS number 38963-95-0) has two hydroxyls in positions 3 and 5 of the furthest benzene the glycosid group (Formula II).

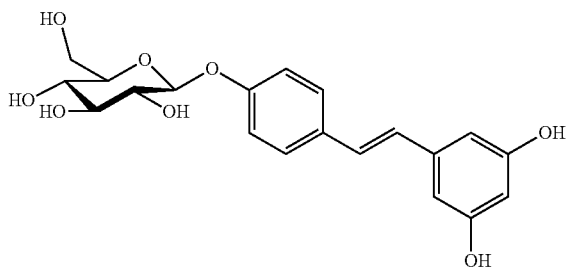

(II)

Polydatin—(2S,3R,4S,5S,6R)-2-(3-hydroxy-5-((E)-4-hydroxystyryl)phenoxy)-6-(hydroxymethyl)tetrahydro-2H-piran-3,4,5-triol—(CAS number 27208-80-6) has two hydroxyls, one in position 3 of benzene adjacent to the glycosid group and one in position 4 of the benzene further from the glycosid group (Formula III).

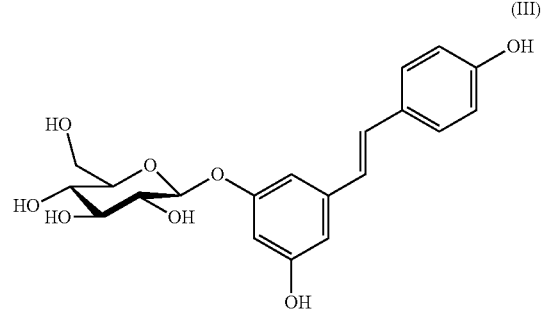

(III)

Astringin—(2S,3R,4S,5S,6R)-2-(4-((E)-3,5-dihydroxystyryl)-2-hydroxyphenoxy)-6-(hydroxymethyl)-tetrahydro-2H-piran-3,4,5-triol—(CAS number 29884-49-9) has three hydroxyls, one in the benzene position 2 adjacent to the glycosid group, one in position 3 and one in position 5 of the benzene further from the glycosid group (Formula IV).

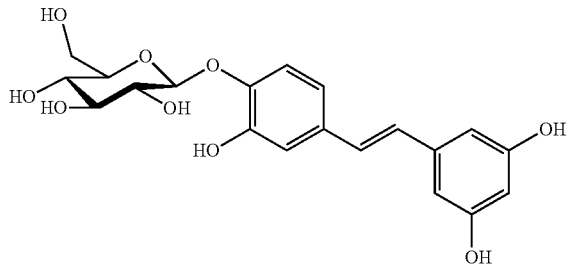

(IV)

The (2R,3S,4S,5R,6S)-2-(hydroxymethyl)-6-(4-((E)-3-hydroxystyryl)phenoxy)tetrahydro-2H-piran-3,4,5-triol—(CAS not available) has a hydroxyl in position 3 of the benzene further from the glycosid group (Formula V).

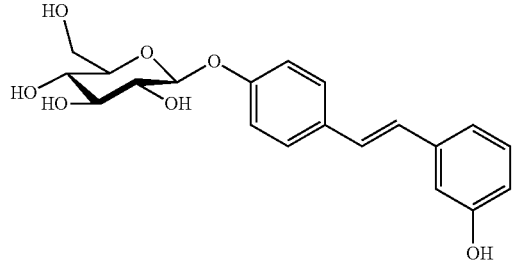

(V)

The compounds represented generically in the formula (I) are present in various concentrations in the natural extracts containing the same, such as for example the pine nut extracts from the genus *Pinus* and the extracts of *Poligonum cuspidatum* (in particular the roots).

According to the present invention, the terms of curcumins and curcuminoids the purified compounds extracted from *Curcuma longa*, their analogues, derivatives and metabolites normally traceable in the *Curcuma longa* rhizome, are meant. Compounds, taken individually or in a mixture, of both natural and synthetic origin, are included. In fact, curcumin is not a single substance but a mixture of congeneric substances. In the following the term curcumins also includes curcuminoids, including cyclocurcumins and hydrocurcumins as defined below, and the related mixtures.

Curcuminoids normally have in common the linear diaryleptanoid structure, with 2 phenol groups variously substituted, linked by a chain with 7 carbon atoms (C6-C7-C6). The 2 phenolic groups are normally bound by α, βunsaturated β-diketone groups. It is also possible that due to internal cyclization the bond is an α, βunsaturated di-hydropyranone group, as in cyclocurcumin (2-(4-hydroxy-3-methoxyphenyl)-6-[(E)-2-(4-hydroxy-3-methoxyphenyl) ethenil]-3,4-dihydro-2H-piran-4-one) or that for the hydrogenation there are no unsaturated bonds, as in idrocurcumins (taken from https://it.wikipedia.org/wiki/Curcuminoidi). They can be used alone or mixed together.

In the following, the term "curcumin" means the combination of Curcumin I, Curcumin II and Curcumin III, preferably used in the following ratios:

| Curcuminoid distribution according to the USP pharmacopoeia ||| 
|---|---|---|
| Substance | Name | Concentration (% w/w) |
| (structure) | diferuloylmethane, circumin or curcumin I | 70-80 |
| (structure) | p-hydroxy cinnamoylferuloylmethane demethoxycurcumine or curcumin II | 15-25 |
| (structure) | p,p-di-hydroxy cinnamoylmethane, bisdemethoxycurcumine or curcumin III | 2.5-6.5 |

According to the present invention, the term "curcumins" is intended to identify both curcumins in the strict sense and curcuminoids, its derivatives and metabolites as indicated above, that can be obtained by extraction from turmeric or by chemical synthesis.

Curcumins according to the invention can be used in the combination of the invention alone or in a mixture with each other. They can be obtained by chemical synthesis or by extraction from natural sources, according to known techniques.

Extracts according to the invention can be prepared following the methods traditionally used in the field of extraction of natural products, known to the persons skilled in the art or as described for example in EP1292319 or in "*Botanicals, a Phytocosmetic Desk Reference*" Frank S. D'Amelio, CRC Press, pgs. 39-48.

The inventors have now found a surprising synergistic effect expressed by the combination of piceids+curcumins, in particular the combination polydatin+curcumin (mixture of Curcumin I, Curcumin II and Curcumin III), in the treatment of tumors of the Central Nervous System and in particular of GBL, when the administration is done through the mouth mucosa and in particular through the sublingual way.

The compositions of the invention are in fact able to induce an unexpected improvement in subjects suffering from CNS tumors of the 3rd and 4th degree. More particularly, it has been experimentally found with studies on humans carried out over a period of five years, that an improvement was reached in controlling the progression of the tumor pathologies with a poor prognosis and a rise of life expectancy which was at least doubled compared to subjects treated with traditional conventional therapies (surgery and/or chemotherapy and/or radiotherapy), so unexpectedly obtaining an almost normal quality of life and at the same time a significant reduction in the size of the tumor masses, as shown by way of example in the Magnetic Resonance images of patients during integrated therapy according to the invention.

The present invention therefore refers to pharmaceutical compositions comprising piceids and curcumins, and in particular the combination of polydatin+curcumin (mixture of Curcumin I, Curcumin II and Curcumin III), in combination with each other for use in the treatment of CNS tumors. The action of piceids regards the inhibition of proliferation, the action of increasing apoptotic activity or the reduction of migration or invasion of malignant glia cells. The action of curcumins mainly concerns an important protein complex as a DNA transcription factor (NF-kB) controller or cytokines that produce cell survival. The main action of this factor occurs on inflammation, "primus movens" of proliferative activity. By maintaining this state, stimulating conditions are created for cell growth, growth of new vessels, and uncontrolled growth. A block of NF-kB means to remove stimuli to edema, inflammation, and growth stimulation. In the case of glioblastoma and especially after surgery or radiotherapy, the use of curcumins would lead to a reduction in inflammatory conditions and consequently a reduction in neoangiogenesis and therefore in the stimulation of uncontrolled cell growth. The inventors have also unexpectedly found that there is a further improving synergistic effect if the mixture of piceids and curcumins is used in combination with at least one anti-edema compound, in particular with plant extracts of *Boswellia serrata*. Such combinations are in fact capable of producing effects even more pronounced than those that would be expected from a simple sum of the ameliorative effects due to the mixture of piceids and curcumins.

Pharmaceutical compositions according to the invention may be administered in combination with surgical treatments and/or anticancer drugs and/or radio/chemo/therapies so as to constitute an Integrated Oncologic Therapy (IOT) and can be administered in a simultaneous, sequential or delayed way compared to the traditional therapies mentioned before.

The compositions of the invention are administered by sublingual or intranasal way. The pharmaceutical forms can be capsules, tablets or pills formulated for absorption through the mouth or nose mucosa, in particular in the sublingual way or in a mouth soluble gel or in aerosol formulations.

The administration of curcumins through the mouth mucosa is further enhanced by the phytosomal formulation, consisting of the combination of the active ingredient with a phospholipid and which also makes it easily permeable at the intestine level, so making this molecule biologically available and with a high percentage of active ingredient in blood.

In another aspect, the composition comprises (% by weight):(polidatin) from about 4.5% to about 7.5%, and more preferably from about 5.5% to about 6.5%, by weight of polidatin; (curcumin) from about 5.5% to about 8.5%, and more preferably from about 6% to about 8%, by weight of curcumin.

To the composition of the invention can be advantageously associated with the administration of anti-edema compounds, preferably in amounts from about 0.0% to about 1.5%, and more preferably from about 1.2% to about 1.4%, by weight.

The active agents are formulated in combination with at least one pharmaceutically acceptable carrier. Such carriers are well known in the art and are generally present in solid, liquid or gel form.

Solid-form pharmaceutical preparations which can be formulated according to the invention include powders, tablets, dispersible granules, capsules and cachets. In general, the preparations in solid form will comprise as a whole from about 5% to about 90% by weight of the active agent.

A solid carrier can be made by one or more substances which may also act as diluents, flavoring agents, solubilizers, lubricants, suspending agents, binders or disintegrating agents of the tablet; they can also be encapsulant materials. In tablets, the active compounds are mixed with a carrier having the necessary binding properties in suitable proportions and compacted to the shape and size desired. Suitable solid supports include magnesium carbonate, magnesium stearate, pectin, starch, gelatin, tragacanth gum, methylcellulose, carboxymethylcellulose, waxes, cocoa butter and the like. The term "preparations" includes the formulation of the active compound with encapsulating materials as per se known carriers, that can provide a capsule in which the active components are included, with or without other adjuvants.

Tablets, powders, capsules and soft capsules can be used as solid dosage forms suitable for oral administration by absorption through the mouth mucosa, in particular in a sublingual way.

The preparations in solid or liquid form may contain, in addition to the active ingredients, flavorings, colorants, stabilizers, preservatives, buffers, sweeteners and natural, dispersants, thickeners, solubilizers and the like. The pharmaceutical preparations can also be in unit dosage form. In this form, the preparations are subdivided in unit doses with appropriate amounts of the active components.

Sublingual tablets are formulated to develop $CO_2$ within the oral cavity. The production of carbon dioxide derives from the reaction of a soluble organic acid with a base. Soluble organic acids can be: citric, malic, tartaric, etc. The soluble bases can be: sodium carbonate/bicarbonate, potassium carbonate/bicarbonate. The formulation is calibrated so that the dissolution of the tablet will also begin with a very small amount of water (saliva) which due to the neutralization of the base acid will give rise to a reaction the effect of which is the formation of further water. Therefore, during production and storage, contact with water and moisture should be avoided.

Water-soluble binders are used (sorbitol, dextrose xylitol, etc.) and anti-caking agents (vegetable magnesium stearate, benzoic acid, adipic acid, etc.). Other excipients are used to improve the taste of the tablets, to limit their bitterness and improve the sweetness and oral sensation of the formulation.

Avoided with care should be excipients which are potentially contraindicated in the literature for cancer patients (for example sugars).

Sublingual tablets are produced in a way similar to the normal swallowable tablets, but however further measures must be followed:
raw materials as already indicated must be kept away from humidity;
where necessary, raw materials that do not have good compressibility must be transformed into granulates.

The final result was to develop a stable immediate release formulation characterized by good taste and rapid disintegration leading to greater absorption and high levels of the active ingredient in the systemic circulation.

Particularly advantageous is a release system based on bioadhesive polymers, as they are suitable for administration in the oral cavity. This release system includes:
the active ingredients;
a bioadhesive polymer, for example selected from polyacrylic acids, polyvinyl alcohol, semi-synthetic cellulose derivatives, hydrophilic derivatives of starch, alginates, pectin, chitosan, polysaccharides, natural rubbers, polyethylene oxides, preferably polyethylene oxides with a molecular weight greater than 600 kDa, more preferably in an equal proportional mixture with a polyethylene oxide with a molecular weight greater than 4000 kDa; and related mixtures; and
a percentage by weight of cyclodextrin (CD), preferably beta-cyclodextrin and its derivatives, more preferably HP-beta-CD and methyl-beta-CD, with respect to the polymer which varies in the range from 0 to 70% by weight, preferably around 50%.

The components are processed with known techniques, such as film casting or other techniques which allow to obtain portioned films suitable for administration in the oral cavity, in particular by a sublingual administration. The films thus obtained are particularly suitable for administration to animals, newborns, infants and the elderly.

According to the invention, the compositions can be realized in such a way as to allow the release of the different active ingredients in a simultaneous, sequential or delayed way.

The compositions according to the invention can be formulated as liposomal formulations with mono- and plurilamellar liposomes, inserted into glucan matrices, based on graphene and combined with nano-carbon particles, so-called Carbon quantum dots (CQDs, C-dots or CDs) (smaller than 10 nm) https://en.wikipedia.org/wiki/Carbon-_quantum_dots.

Another advantageous method of administration is spray or aerosol in the case of intranasal administration in particular.

According to the invention, the compositions can be used alone or in combination with other active ingredients known to be effective as anticancer or antineoplastic and/or radio-protective and/or other drugs administered before or after surgery to reduce or remove the tumor.

Among antineoplastic agents can be mentioned those belonging to families of antineoplastic agents: Temozolomide, Dacarbazine, Lomustine, Cisplatin, or to those of anti-angiogenic agents: Trastuzumab primarily.

Radiotherapy "whole brain" technologies or gamma-knife radiosurgery or tomotherapy, or hadrotherapy or stereotactic radiosurgery (cyberknife) can be used in combination with compositions of this invention.

In a preferred embodiment, the composition is administered in a daily dose of at least a total of about 500 mg of active products (in single or fractionated dose during the day).

An effective amount will generally comprise from about 2 mg to about 4 mg of polydatin and from about 2 mg to about 5 mg of curcumin per kilogram of body weight of the patient per day. This effective amount may vary depending on the physical state of the patient and other factors well known in the art. Furthermore, this dose of active agent can be administered in a single unit or in multiple dose units to provide the desired therapeutic effect.

In another aspect, the composition is administered daily for at least 6 weeks (during the Radiotherapy application cycle), preferably for the rest of the patient's life. Preferably two administration intervals are identified, a periodicity relative to the acute phase and a periodicity relative to the maintenance phase. During the acute phase, which can last up to 1 year, amounts of at least 500 mg of the composition are administered. During the maintenance phase, which can last for the rest of the patient's life, quantities of 300 mg of the composition are administered.

The acute phase generally concerns the period of treatment with radiotherapy (from 15 to 30 applications in total) and with cycles of chemotherapy (with the drugs indicated above) for a maximum period of 1 year (6-12 cycles of Temozolomide).

The maintenance phase generally concerns the follow-up period in which conventional treatments are not administered.

A dose of 1 sachet×2 times a day will be given. The quantity of active principles and doses vary depending on the host treated and the particular mode of administration. It is understood, however, that a specific dose level for any particular patient will depend upon a variety of factors, including the activity of the specific compound employed, age, body weight, general health, sex and diet of the patient, administration time; the excretion rate; the combination of drugs administered, the severity of the particular disorder to be treated and the form of administration.

The inventors have examined the action, on a group of over 70 patients with glioblastoma, of pharmaceutical compositions containing:
polidatin+curcumin according to the invention plus excipients with administration ways other than the sublingual ones
polidatin+curcumin according to the invention plus excipients in sublingual way.

Said combinations were also tested on pediatric subjects between 4 and 15 years, also in this case with a positive outcome.

The result of the simultaneous administration of the two molecules, even after the radio chemotherapeutic treatment, leads to a reduction—radiologically demonstrated—of the tumor area in the patients due to the synergy of the antitumor activity of polydatin (induced apoptosis of GBL cells) and anti-angiogenetic-anti-inflammatory of curcumin by sublingual way, as shown in the attached figures.

The sublingual pathway, together with the intranasal one, is one of the enteral ways a drug can be administered; instead of being swallowed, the drug can be placed in the sublingual region or between the gingiva and cheek so that it is absorbed into the mouth or sprayed inside the nose. The sublingual venous circulation is tributary of the superior vena cava and this guarantees that the drug reaches the systemic circulation more quickly (including the cerebral circle); in this way the drug arrives in the systemic circulation by skipping the hepatic metabolism. From this a rapid onset of the effect is derived, as the absorption is very rapid due to the thinner absorption surface than the intestinal one and as the drug has a higher lipo-solubility than that of the intestinal absorbed drugs (necessarily considering that the absorption surface is far less extended).

Data presented by the inventors are clinical data certified by Public Control Health Authorities and therefore they can be used in the context of international protocols for the treatment of human GBL.

For comparison the experimental data in animals present in literature refer to a grafted tumor, totally different from a spontaneous onset in humans, due to chronic inflammatory facts and/or immune deficiency; however the experimental data of tumors in the mouse, as already discussed in the part of the description relating to the known art, cannot be transferred in any way to the therapeutic practice in humans.

The present invention relates to a method of sublingual administration and exploits the natural lipo-affinity of molecules chosen with respect to the oral/sublingual mucosa, where a particular vascularization allows a rapid diffusion in the blood circulation proximal to the cerebral circulation; therefore the drug reaches the systemic circulation more quickly, including the brain, by skipping the entero-hepatic circle where the molecules can undergo metabolic transformations such as those that occur with an oral or intra-peritoneal administration.

It is assumed that the intrinsic characteristics of curcumin and polydatin (compared to the more known resveratrol, which is not absorbed in the mucosa—not even the intestinal one)—allow the mixture of components to favor a local emulsion in contact with the saliva, that absorbs quickly by diffusion in the capillary micro-circulation of the oral mucosa.

In addition, still according to a hypothesis of the authors, the effect of the molecules is not only anti-cancer but it could be associated to factors already proven having a natural immunity for polydatin, besides the already demonstrated antitumor effect which is combined with an anti-inflammatory effect due to the inhibition of lipid peroxidation (ROS production during radiotherapy).

The following examples are to be considered illustrative and not limiting of the scope of the invention. Unless otherwise indicated, all percentages are in % by weight.

EXAMPLES

Examples of Compositions Containing Polydatin+Curcumin.

Process for Preparing Polydatin+Curcumin Sublingual Tablets

Sublingual tablets are formulated to develop $CO_2$ within the oral cavity. The production of carbon dioxide derives from the reaction of a soluble organic acid with a base. Soluble organic acids can be: citric, malic, tartaric, etc. Soluble bases can be: sodium carbonate/bicarbonate, potassium carbonate/bicarbonate. The formulation is calibrated so that the dissolution of the tablet will also begin with a very small amount of water (saliva) which due to the neutralization of the base acid will give rise to a reaction the effect of which will be the formation of other water. Therefore, during production and storage, the contact with water and moisture must be avoided.

Water-soluble binders are used (sorbitol, dextrose xylitol, etc.) and anti-caking agents (vegetable magnesium stearate, benzoic acid, adipic acid, etc.). Other excipients are used to improve the taste of the tablets, limit their bitterness and improve the sweetness and oral sensation of the formulation.

Carefully avoided must be excipients which are potentially contraindicated in the literature for cancer patients (e.g. sugars).

The sublingual tablets are produced in a similar way to the normal swallowable tablets, however further measures should be followed:

the raw materials as already indicated must be kept away from moisture;

where necessary, raw materials that do not have good compressibility must be transformed into granulates.

The final result is to develop a stable immediate release formulation characterized by good taste and rapid disintegration which leads to greater absorption and high levels of the active ingredient in the systemic circulation.

Example of Sublingual Polydatin-Curcumin Formulation:

Sublingual POLYDATIN-CURCUMIN 30 sublingual tablets 400 mg D.10

Composition of the formula structured in phases:

| COMPONENTS | % | Mg |
|---|---|---|
| Sorbitol | 40 | 160 |
| Microcrystalline Cellulose (Charge Agent) | Qs to 100 | Qs to 400 |
| Sodium Bicarbonate (anti-aggregator) | 10 | 40 |
| Tartaric acid (anti-aggregator) | 5 | 20 |
| Erythritol (anti-aggregator) | 5 | 20 |
| Glicaril Di-beenate (Charge Agent) | 4 | 16 |
| Vegetable Magnesium Stearate (anti-aggregator) | 1 | 4 |
| Stevia Powder (glycosides) (sweetener) | 1 | 4 |
| Curcumin | 15.38 | 61.53 |
| Polydatin | 4.62 | 18.47 |

Example 2

Effervescent Tablets

Amount of characterizing elements:
Polydatin 60 mg
Curcumin 200 mg
Ingredients:
Acidifier: anhydrous citric acid; acidity corrector: sodium bicarbonate; maltodextrins; aroma; sweeteners: Stevia glycosides and sorbitol; dye: beta-carotene.

Example 3

Drinkable Stickpack Gel

Amount of characterizing elements:
Polydatin 60 mg
Curcumin 200 mg
Ingredients:
Polydatin (for example from *Fallopia Japonica* plant), Curcumin (from *Curcuma* for example rizome), emulsifier: beta-cyclodextrin, thickener: xanthan gum, Orange flavor, Acidifier: citric acid; Preservative: Potassium sorbate, Sweetener: Erythritol, Water.

Clinical Study

Improvement of the Quality of Life and Survival in Patients with Glioblastoma in Conventional Treatment with Integration of Natural Substances Introduction High grade glial tumors are considered one of the most aggressive diseases with the worst prognosis. The average survival time of patients with glioblastoma, the most aggressive malignant glia tumor, is from 9 to 12 months and for malignant oligo-dendroglioma is about 2 years. Recurrence after surgical treatment is very common even in the case of chemotherapy and radiotherapy treatment. This study is aimed at exploring the efficacy of natural substances that are the subject of the present invention on selected patients with glioblastoma and to study the utility of the combined treatment, with natural curcumin, polydatin and *Boswelia serrata* in combination with the conventional treatments of glioblastoma.

Materials and Methods

GBL has an incidence of 3-4 cases per 100.000 and therefore the sample under study is highly representative as it concerns a population of about 2 million people.

We have retrospectively studied 72 patients in a Roman hospital, suffering from glioblastoma cancer, between September 2012 and March 2017. We derived patient data from the review of patients' clinical and outpatient records and from direct patient follow-up visits. The main inclusion criteria were the following: 18 years or more; histological evidence of glioblastoma and clinical and radiographic evidence of brain cancer.

All patients who had been diagnosed radiologically with a probable neoplastic lesion of cerebral origin underwent surgical biopsy for histological diagnosis and, when possible, also surgery for neoplasm removal. Subsequently all patients underwent 30 sessions of radiant treatment (whole-brain radiotherapy) in association with a first-line pharmaco-chemotherapy: temozolomide (dose: 80 mg/m$^2$ of body surface). When possible, temozolomide was continued 1 month after the end of the treatment, 1 daily administration for 5 days, every 28 days.

Since the patients underwent integrated treatment (IOT) we began to monitor all the vital parameters (hematological and urinary tests) and the evolutions from the point of view of the instrumental exams (CT and MRI). Many of them began treatment with the composition of the invention from the beginning of the diagnosis. Some instead started the IOT in the various phases of conventional treatment.

The administration has a range of 3 mg/day/kg of body weight of polydatin, while for curcumin 200 mg, in a single pharmaceutical formulation (gel and/or mouth soluble tablet, adhesive film) of 80 mg polydatin and 200 mg curcumin administered in a single or fractionated daily dose.

Results

The clinical data obtained are statistically significant and based on the methods established by Evidence Based Medicine as regards the survival evaluation, an on-off result not foreseen in the epidemiology of GBL, supported by the Oncology Ethics Committee of the Lazio Region (unpublished data).

The unexpected results were a reduction in the undesirable effects of radiotherapy (reduced post-actin edema); reduced post-radiotherapy fatigue. Also a minor reduction in the platelet count was noted (which is frequent with the use of Temozolomide) as well as in white and red blood cells. These results gave the possibility to continue the chemotherapy treatment without interruption and for all the desired cycles.

A total of 72 patients with glioblastoma cancer were included in this study. The average age was 57 years (Range, 12-79 years). There were more males (43; 59%) than females (30; 41%). Of these patients, 66 (91.7%) had undergone surgery with complete resection in 28 cases (42.4%). 69 patients (95.8%) had undergone radiotherapy. 6 patients (8.3%) had not received any chemotherapy, 53 (73.6%) patients had received chemotherapy, 52 of them with temozolomide and only one with Nimotuzumab plus vinorelbine, 11 (15.3%) patients had received a second treatment, consisting mainly of fotemustine, while 2 patients (2.8%) had received a third treatment (1 BCNU Carmustine plus PCV conjugated pneumococcal vaccine and 1 rituximab). They were visited for the first time in our center after an average time of 3.9 months from the diagnosis that ranged from 10 days to 14 months. At the time of the first visit 31 (43.1%) patients had used corticosteroids.

Of these 72 patients, 7 (9.7%) had never started the therapy and 5 more (6.9%) patients were poorly adherent to the IOT protocol (in the sense that they did not regularly follow medical prescriptions).

Univariate Analysis and Multivariate Analysis

The overall survival (Overall Survival—OS) of the entire series was 13.3 months (95% confidence interval CI: 7.3-19.3), for the 65 treated patients it was 16.3 months (95% CI: 0.2-32.4). The series of 60 patients who were really adherent to the therapy had achieved an average OS of 25.4 months (95% CI: 8.3-42.5). The one-year survival rate of the entire series was 53.1%, for the 65 patients treated it was 55.4%.

The series of 60 patients who were really adherent to the therapy had achieved a one-year survival rate of 59.0%. No difference in survival was observed with respect to gender, age, number of previous chemotherapy treatments. In fact, the one-year survival rate was 51.9% for males and 59.1% for females. A one-year survival rate was 53.8% for younger patients (<57 years) and 57.0% for older patients. A one-year survival rate was 58.0% for patients who had received only a chemotherapy treatment and 56.3% for patients who received two or three treatments. Patients who had taken corticosteroids had a one-year survival rate of 58.7% and for those who had not taken corticosteroids the rate was 50.6%.

The overall average survival of the whole series was different: for patients who had not undergone surgery (one-year survival rate of 18.3%), for patients who had undergone complete surgery (one-year survival rate of 74.0%) and for patients who had only undergone biopsy (one-year survival rate of 56.4%). The average OS from the diagnosis was 34.4 months (95% CI: 18.1-40.8), with a one-year survival rate that was 82.4% and for two years the survival rate was 54.2%.

Data Update

The sample of survivors is highly significant with a survival permanence now higher as a median than 55 months.

The current survival result is over 25% if we consider the group closely adherent to the protocol (60 out of 72 patients), otherwise the total of the study is 11%. By contrast, the international 5-year figure is only 3%.

Conclusions

Brain tumors such as glioblastoma have a poor prognosis and, unfortunately, patients rarely have a long survival even when treated with chemotherapy and radiotherapy. The use of a conventional multimodal treatment with the combination of the invention is a useful aid to extend the survival of patients with brain tumors and ensures a good quality of life.

Through the data presented here, the inventors have found a surprising increase in the survival of patients treated for glioblastoma, who are still alive, as well as an improvement in their symptomatology.

The invention claimed is:

1. A method for treating a tumor comprising administering to a patient in need thereof a combination of polydatin and curcumin, wherein the tumor is selected from the group consisting of astrocytomas, oligodendrogliomas, ependymomas, anaplastic astrocytomas and glioblastomas.

2. The method of claim 1, wherein curcumin consists of a mixture of Curcumin I, Curcumin II and Curcumin III.

3. The method of claim 1, wherein the polydatin and curcumin are formulated as a pharmaceutical or a nutraceutical composition.

4. The method of claim 1, wherein the polydatin and curcumin are is administered intranasally or sublingually.

5. The method of claim 1, wherein polydatin is combined or formulated with one or more resveratrolosides of general formula (I):

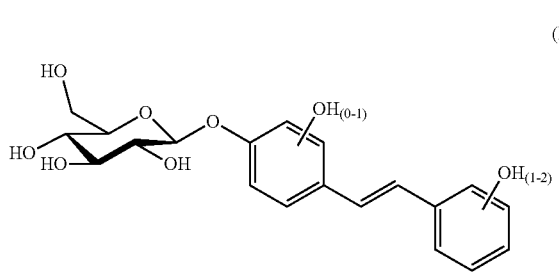

(I)

6. The method of claim 5, wherein the resveratrolosides are selected from the group consisting of:
Resveratroloside, Polydatin, Astringin, (2R, 3S, 4S, 5R, 6S)-2-(hydroxymethyl)-6-(4-((E-3-hydroxystyryl)phenoxy)-tetrahydro-2H-piran-3,4,5-triol, and corresponding mixtures; and curcumins are selected from: curcumin I, curcumin II, curcumin III, hydrocurcumin, cyclocurcumin, and corresponding mixtures.

7. The method of claim 1, wherein the polydatin or curcumin is formulated in solid, liquid, gel, aerosol form; as liposomal formulation with mono- and plurilamellar liposomes, as phytosome; or formulated with bioadhesive polymers, with arrays of glucans or based on graphene, or combined with carbon nano-particles.

8. The method of claim 1, wherein the polydatin and curcumin are formulated in a single composition comprising from about 4.5% to about 7.5% by weight of polydatin; and from about 5.5% to about 8.5% by weight of curcumin, and a pharmaceutically acceptable carrier.

9. The method of claim 1, wherein:
(a) the polydatin and curcumin are administered in combination with: an active ingredient selected from the group consisting of: anti-edema compound, optionally in an amount ranging from about 1.2% to about 1.5% by weight; anticancer drugs; antineoplastic drugs, optionally Temozolomide, Dacarbazine, Lomustine, or Cisplatin; antiangiogenic agents, optionally Trastuzumab; radioprotective agents; drugs administered before or after surgery to reduce or remove the tumor; and combinations thereof; or
(b) administration of the polydatin and curcumin is accompanied by: radiotherapy, optionally whole brain radiotherapy technology; gamma-knife radiosurgery; tomotherapy; hadrotherapy; stereotactic radiosurgery (Cyberknife), or a combination thereof.

10. The method of claim 1, wherein the polydatin and curcumin are administered in a daily dose of at least about 400 mg total of active compounds; or are administered in a dose from about 2 mg to about 4 mg of polydatin and from about 2 mg to about 5 mg of curcumin per kilogram of body weight of the patient per day.

11. The method of claim 1, wherein the polydatin or curcumin are administered in a single unit or several dosage units per day.

12. The method of claim 1, wherein the polydatin and curcumin are administered:
(a) daily for at least 6 weeks during treatment with radiotherapy and chemotherapy;
(b) for at least 1 year, optionally with 6-12 cycles of Temozolomide,
(c) for the rest of the patient's life;
(d) with two periods of administration, a periodicity relative to an acute phase and a periodicity relative to a maintenance phase;
(e) during an acute phase, or optionally for 6 months to 1 year;
(f) in amounts of at least 500 mg per day in a single or fractionated dose; or
(g) during a maintenance phase, or optionally for the rest of the patient's life, or optionally in an amount of at least 300 mg administered in a single or fractionated daily dose.

13. The method of claim 1, wherein the polydatin and curcumin are administered as a pediatric composition or are formulated as a pediatric composition or are dosaged as a pediatric composition.

14. The method of claim 1, wherein the curcumin is combined or formulated with, or comprises, one or more curcumins having:
(a) a linear diarylheptanoid structure, with 2 phenolic groups linked by a chain with 7 carbon atoms;
(b) a cyclized structure for inner cyclization or having an hydrogenated structure without unsaturated bonds; or
(c) a mixture of (a) and (b).

15. The method of claim 7, wherein the composition comprises from about 5.5% to about 6.5% by weight of polydatin.

16. The method of claim 7, wherein the composition comprises from about 6% to about 8% by weight of curcumin.

17. The method of claim 1, wherein the composition comprises: from about 5.5% to about 6.5% by weight of polydatin; from about 6% to about 8% by weight of curcumin; or, from about 5.5% to about 6.5% by weight of polydatin and from about 6% to about 8% by weight of curcumin.

* * * * *